US00PP15589P2

(12) United States Plant Patent
Bessho

(10) Patent No.: US PP15,589 P2
(45) Date of Patent: Feb. 22, 2005

(54) ***CALIBRACHOA* PLANT NAMED 'KAKEGAWA S62'**

(50) Latin Name: ***Calibrachoa* species**
Varietal Denomination: Kakegawa S62

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 29 days.

(21) Appl. No.: 10/802,071

(22) Filed: Mar. 15, 2004

(51) Int. Cl.[7] ..... A01H 5/00
(52) U.S. Cl. ..... Plt./263
(58) Field of Search ..... Plt./263, 356

*Primary Examiner*—Kent Bell
(74) *Attorney, Agent, or Firm*—Jondle & Associates P.C.

(57) ABSTRACT

'Kakegawa S62' is a new variety of *Calibrachoa* plant. This new variety has red petal lobes with purple petal lobe veins and dark green foliage.

1 Drawing Sheet

Genus/species: *Calibrachoa* species.
Varietal denomination: 'Kakegawa S62'.

BACKGROUND OF THE INVENTION

'Kakegawa S62' originated from a hybridization made in November 1998 in Kakegawa, Japan. The female parent was a *Calibrachoa* 'Colorburst Cherry' (U.S. Plant Pat. No. 12,504). The male parent was a *Calibrachoa* breeding line, with a deep rose colored flowers, mounding habit and short internode length known as 97-1176 (not patented).

In February 1999, $F_1$ seed from this cross was sown and later transplanted outdoors in Kakegawa, Japan. The $F_1$ plants were either rose or red in flower color. Three plants were selected for their red flower color and intercrossed to create an $F_2$ generation. In August 1999, 100 lines of $F_2$ seed were sown and later transplanted outdoors. The $F_2$ plants ranged from extra compact to mounding in habit, as well as being either rose or red in flower color. Two, single-plant selections from the $F_2$ generation were selected for their red flower color and extra compact habit and vegetatively propagated. In February 2002, the two selections were evaluated in 9 cm hanging pots in a greenhouse as well as in an open field. One selection was chosen based on trial results.

The selection was further evaluated from new vegetative plants in Salinas, Calif. during 2003. The selection was subsequently named 'Kakegawa S62'. 'Kakegawa S62' was asexually reproduced by stem cuttings in Salinas, Calif. and was determined to reproduce true to type in successive generations of asexual propagation.

DESCRIPTION OF PHOTOGRAPH

This new *Calibrachoa* plant is illustrated by the accompanying photograph which shows blooms and foliage of the plant in full color. The colors shown being are as true as can be reasonably obtained by conventional photographic procedures.

DESCRIPTION OF THE GENUS *CALIBRACHOA* LLAVE & LEX

Figure 1:
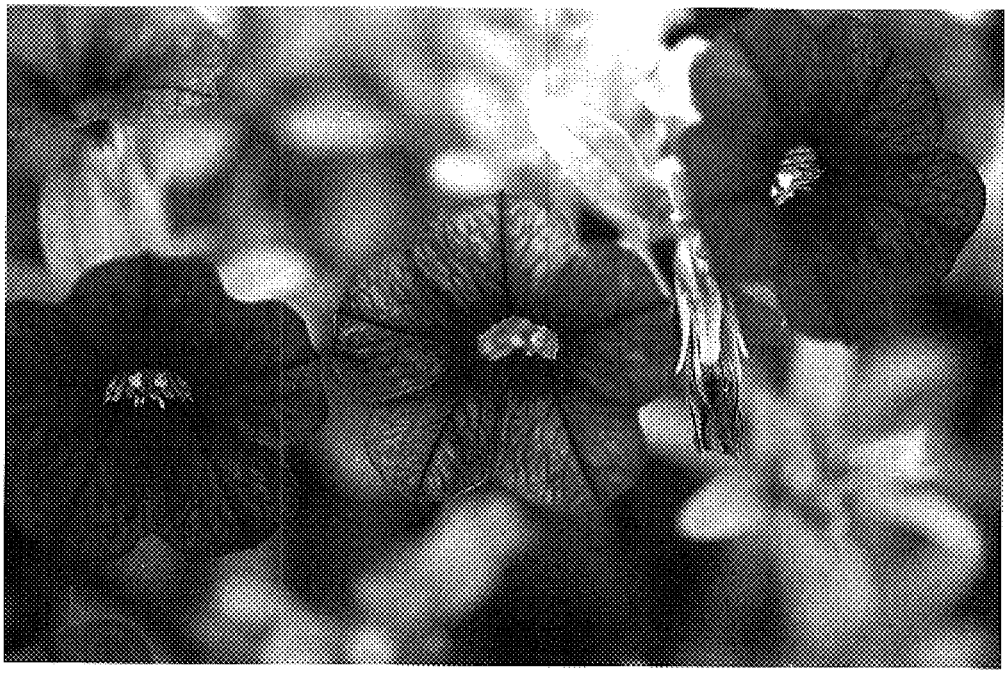
FIG. 1 shows a close-up view of flowers.
Figure 2:
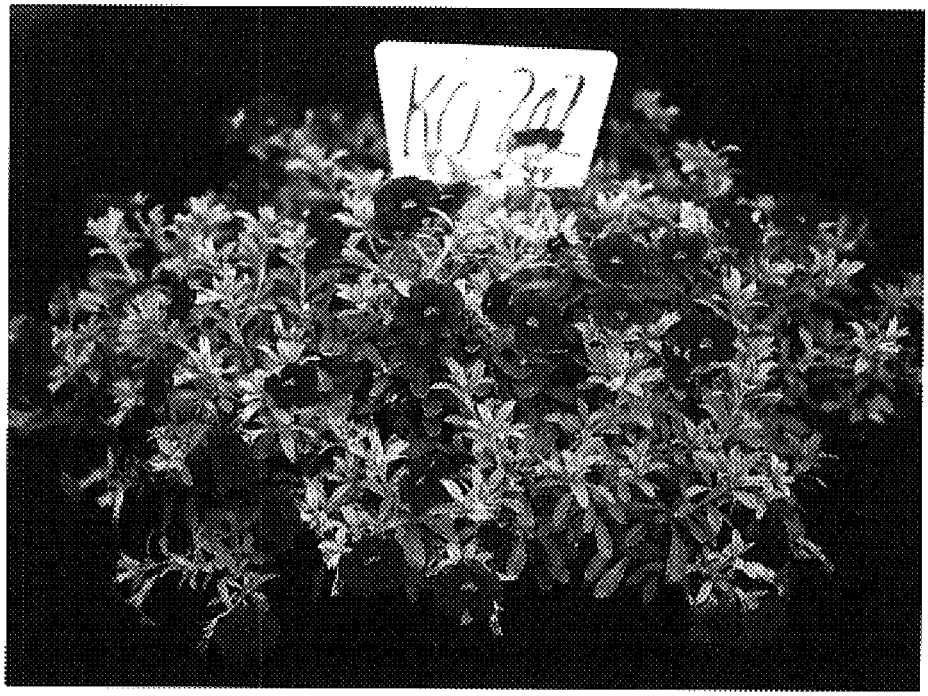
FIG. 2 shows the entire plant (known as K0-202 during testing).

The genus *Petunia* was originally established in 1803 by A. L. Jussieu, who described both *P. parviflora* and *P. nyctaginiflora* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida*, the Garden *Petunia*, and the inter-relationship of several species classified as *Petunia*. These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the *Petunia* genus, Wijsman and J. H. de Jong proposed transferring the 14 chromosome species to the genus *Stimoryne*. Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990, Wijsman had transferred several species, including *P. parviflora* (=*C. parviflora*) to *Calibrachoa*, originally established by Llave and Lexarza in 1825. *Calibrachoa parviflora* (=*C. mexicana* Llave & Lexarza) is now the type species for the genus *Calibrachoa*.

Classification of the current *Petunia* and *Calibrachoa* species is still in progress. New species are also being identified. Consequently, a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, a single outermost petal covers the other four, radially folded and terminally contorted petals. *Calibrachoa* flower buds are flat with all five petals linearly folded and the two lower petals forming a cover around the three other petals and fused together.

ENVIRONMENTAL CONDITIONS FOR PLANT GROWTH

The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 DIP 'N GROW: 9 water) root-inducing solution immediately prior to sticking into the cells trays. Cuttings were stuck into plastic cell trays having 98 cells and containing a moistened peat moss-based growing medium. The cuttings were misted with water from overhead for 10 seconds every 30 minutes until sufficient roots were formed.

Rooted cuttings were transplanted and grown in 20.0 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

DETAILED DESCRIPTION OF THE NEW PLANT

Data below collected on plants four months from rooted cutting and transplanted into 20.0 cm diameter pots. The following traits and characteristics describe the new variety.

Classification:
- *Family.*—*Solanaceae.*
- *Species.*—*Calibrachoa* sp.
- *Common names.*—*Calibrachoa.*

Parentage:
- *Female parent.*—*Calibrachoa* 'Colorburst Cherry' (U.S. Plant Pat. No. 12,504).
- *Male parent.*—Breeding line 97-1176 (not patented).

Growth:
- *Habit.*—Decumbent.
- *Height.*—13.0–15.0 cm.
- *Spread.*—40.0–45.0 cm for one plant when grown in a 20.0 cm diameter pot.
- *Life cycle.*—Perennial.
- *Form.*—Branching, dense, compact (shorter internode lengths).
- *Time to produce a rooted cutting.*—6 weeks.
- *Time to bloom from propagation.*—10 weeks.
- *Flowering requirements.*—Will flower so long as day length is greater than 12 hours and temperatures exceed 13° C.
- *Resistance/susceptibility.*—Excellent resistance to rain, heat and drought. Will not tolerate temperature below 10° C. Plants are susceptible to *Botrytis*, powdery mildew, various stem and root rots and certain viruses, like Tobacco Mosaic Virus and Impatiens Necrotic Spotted Virus. Plants can be infested with aphids, leafminer, whitefly and various *Lepidoptera.*

Stems:
- *Stem color.*—RHS 143C (yellow-green).
- *Anthocyanin color.*—None.
- *Pubescence.*—Heavy.
- *Pubescence color.*—RHS N155A (white).
- *Stem description.*—Round.
- *Stem length.*—2.0 cm–2.5 cm.
- *Stem diameter.*—1.5–1.8 mm.
- *Internode length.*—0.5–1.0 cm.

Leaves:
- *Leaf arrangement.*—Alternate.
- *Leaf shape.*—Elliptical.
- *Leaf tip.*—Mucronate.
- *Leaf base.*—Decurrent.
- *Leaf margin.*—Entire.
- *Leaf surface.*—Rough, dull.
- *Leaf length.*—2.8–3.2 cm.
- *Leaf width.*—0.9–1.1 cm.
- *Leaf variegation.*—None.
- *Leaf color.*—Upper: RHS 137A (green); lower: RHS 138B (green).
- *Leaf surface pubescence.*—Slight.
- *Leaf surface pubescence color.*—RHS N155B (white).
- *Petiole length.*—2.0.
- *Petiole color.*—RHS 138B (green).
- *Venation.*—Pinnate.

Flowers:
- *Inflorescence type.*—Solitary.
- *Flowering habit.*—Indeterminate.
- *Duration of flower life.*—5 days.
- *Shape.*—The flowers are funnel shaped with five fissures.
- *Flower depth.*—2.0 cm–2.5 cm.
- *Floral tube length.*—1.2 cm–1.5 cm.
- *Floral tube diameter.*—0.4 cm–0.5 cm.
- *Flower diameter.*—2.5–3.0 cm.
- *Calyx.*—5 sepals, free.
- *Sepal shape.*—Lanceolate.
- *Sepal apex.*—Mucronate.
- *Sepal margin.*—Entire.
- *Sepal color.*—RHS 143A (green).
- *Bud shape.*—Ovate.
- *Bud length.*—1.5 cm–1.7 cm.
- *Bud diameter.*—0.3 cm–0.4 cm.
- *Bud surface.*—Pubescent.
- *Bud color.*—RHS 144B (yellow-green).
- *Peduncle length.*—1.0–1.5 cm.
- *Peduncle color.*—RHS 144B (yellow-green).
- *Ovary.*—Superior.
- *Pistil number.*—1.
- *Stigma color.*—RHS 149A (yellow).
- *Style color.*—RHS 149B (yellow-green).
- *Corolla.*—5 petals, fused.
- *Petal shape.*—Spatulate.
- *Petal apex.*—Truncate.
- *Petal margin.*—Entire.
- *Petal pubescence.*—Glabrous.
- *Petal size.*—2.2–2.5 cm×1.2–1.5 cm.
- *Petal color.*—Lobes: upper RHS 66A (red-purple) with RHS 61A (red-purple) veins; lower RHS N66D (red-purple) with RHS N200A (brown) veins; Corolla tube: inner RHS 9A (yellow) with RHS N200A (brown) veins; outer RHS 5C (yellow) with RHS N200A (brown) veins.
- *Stamen number.*—5, free.
- *Stamen color.*—RHS 150C (yellow-green).
- *Pollen color.*—RHS 10A (yellow).
- *Fragrance.*—Absent.
- *Seed production.*—None.

COMPARISON WITH MOST SIMILAR VARIETY

'Kakegawa S62' is a distinct variety of *Calibrachoa* owing to its short internode length, which leads to a compact growth habit and red petal lobe color with purple lobe veins. 'Kakegawa S62' is most similar to the variety 'Colorburst Violet' (U.S. Plant Pat. No. 12,086); however, there are differences as shown in Table 1 below.

TABLE 1

| | 'Kakegawa S62' | 'Colorburst Violet' |
|---|---|---|
| Internode Length | 0.5–1.0 cm | 1.5–2.0 cm |
| Petal Color Upper | Upper petal color is RHS N66A (red-purple) with RHS 61A (red-purple) veins and an inner base of RHS 9A (yellow). | Upper petal color is RHS 57A (red-purple) with vein color of RHS 202A (black) with purple tinge; secondary vein petal color is RHS 81C (purple-violet). |

Some differences between 'Kakegawa S62' and its parental lines are shown in Table 2 below.

TABLE 2

| Characteristic | 'Kakegawa S62' | Male (97-1176) | Female ('Colorburst Cherry') |
|---|---|---|---|
| Petal Color Upper | RHS 66A (red-purple) | Deep rose | RHS 66A (red-purple) |
| Habit | Decumbent | Mounding | Decumbent |
| Internode Length | 0.5–1.0 cm | 0.5–1.0 cm | 1.0–1.7 cm |

What is claimed is:

1. A new and distinct cultivar of *Calibrachoa* plant as shown and described herein.

* * * * *